United States Patent [19]
Jensen et al.

[11] 3,963,918
[45] June 15, 1976

[54] IDENTIFICATION DEVICE FOR MACHINE MOULDED PRODUCTS

[75] Inventors: Claes-Göran Jensen, Malmo; Lars Olof Hansson, Oxie, both of Sweden

[73] Assignee: Aktiebolaget Platmanufaktur, Malmo, Sweden

[22] Filed: June 17, 1974

[21] Appl. No.: 479,647

[30] Foreign Application Priority Data
June 21, 1973 Sweden............................. 7308779

[52] U.S. Cl............................ 250/223 B; 250/216; 250/568; 356/196
[51] Int. Cl.²........................................ G01D 21/04
[58] Field of Search................ 250/223 B, 216, 566, 250/568, 555; 356/240, 196, 198

[56] References Cited
UNITED STATES PATENTS

| | | | |
|---|---|---|---|
| 3,415,997 | 12/1968 | Vinzelberg et al.................. | 356/197 |
| 3,588,514 | 6/1971 | Simpkins............................ | 250/227 |
| 3,662,181 | 5/1972 | Hercher et al. ............. | 250/223 B X |
| 3,687,559 | 8/1972 | Fischer .............................. | 356/240 |
| 3,745,314 | 7/1973 | Mathias et al............... | 250/223 B X |

*Primary Examiner*—Walter Stolwein
*Attorney, Agent, or Firm*—Hane, Baxley & Spiecens

[57] ABSTRACT

Apparatus for identifying which of a plurality of moulds moulded a particular container includes such moulded containers with coded combinations of lens members in their bottom, the lens members being illuminated to focus light to an optical system terminating at a photosensitive device which emits pulses as the lens members are sequentially scanned.

5 Claims, 10 Drawing Figures

FIG. 2A
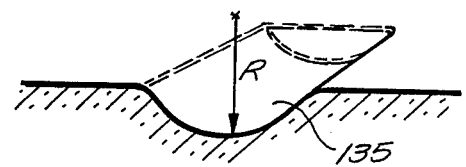
FIG. 2B
FIG. 3
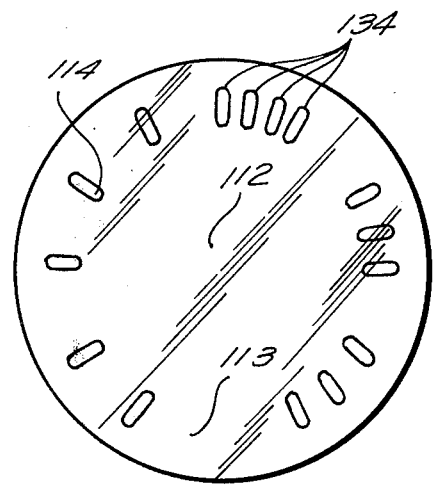

IDENTIFICATION DEVICE FOR MACHINE MOULDED PRODUCTS

The present invention relates to a device for automatic identification of products manufactured by different machine moulds.

In the manufacture of machine moulded products the moulding process proper is often so slow that many units, each often comprising several mould sections, have to work in parallel in order to feed one productionline, which for economical reasons must be operated at a relatively high speed. If one thus wishes to utilize automatic quality control with such a line it becomes necessary to be able to quickly and accurately identify the particular mould section from which a certain product originates when a fault on same product has been discovered.

This requirement is present e.g. in the package industry, which often at high speed manufactures products of glass, tin, plastic, paper or combinations of those materials.

At present the identification of the package is done by means of manual handling in combination with visual reading of mould numbers.

The object of the present invention is thus to obtain an automatic mould number reader, which is suitable for use with a fast running manufacturing line and which is directly suited for co-operation with a computer such that outgoing information from the number reader is preferably binary coded.

This object is achieved by bringing the package, e.g. a bottle, to stand still at an inspection station by means of an advancing means during a certain short time. When manufacturing bottles the line moves with a speed of 1–5 units per second. As a result the time during which the mould number reading must take place is reduced to one or some tenth of a second. At the inspection station the bottle is then illuminated with light, which after reflection or wall penetration hits a light sensitive receiver. Marks or uneventies in the material will then be registered. When reading mould numbers on bottles of transparent glass a lamp with its lens system may, e.g. be mounted such that a directed beam enters through the bottle neck and illuminates the bottom of the bottle, which is then preferably provided with negative or positive lenses integrated in bottle material. These lenses may thus be rotation symetrically disposed, such that a rotating and reading receiver underneath the bottom of the bottle quickly may read the light deflection of the lenses and emit pulses. The angular position of the bottle then may be determined by the fact that the bottom of the bottle is provided with a particular lens combination or starting mark where the reading is to commence. Besides, the rotation apparatus of the reading device must be equipped with a means for registering the rotational movement of the number reader e.g. by induction pulses from a surrounding peripheral cog-wheel or by a rim flange with holes for optical registration.

By using a suitable code, e.g. BCD-code, the computer will receive a combination of mould number pulses, the position of which will be determined by means of the continually received positional pulses. The computer may thus be made to count a certain number of positional pulses after the start signal and then read the digit pulse input, which then will be either high or low. This step may then be repeated a number of times, during one revolution, the number of steps thus being dependent upon the number of generated positional pulses every turn divided by the number of pulses between every reading.

According to a particular embodiment of the invention it has been shown advisable to use 240 pulses per turn and 8 pulses between every reading, i.e. 12 degrees between every character in the bottom of the bottle and thus a maximum of 30 characters along the rotational perephery.

By letting the reader complete two or more turns the reliability may be increased. It is hereby possible to use a so called self-correcting code with inserted parity characters.

The features of the present invention are further defined by the appended claims.

The present invention will also be shown with certain examples which will be described in connection with attached drawing, where:

FIGS. 1A and 1B show respectively a sectional view of a rotating, optical mould number reader and an enlarged section thereof.

FIGS. 2A and 2B respectively show a cylindrical concave and a cylindrical convex lens formed in the bottom of a bottle;

FIG. 3 shows a bottom of a bottle with lenses;

Figures 1A, 1B:
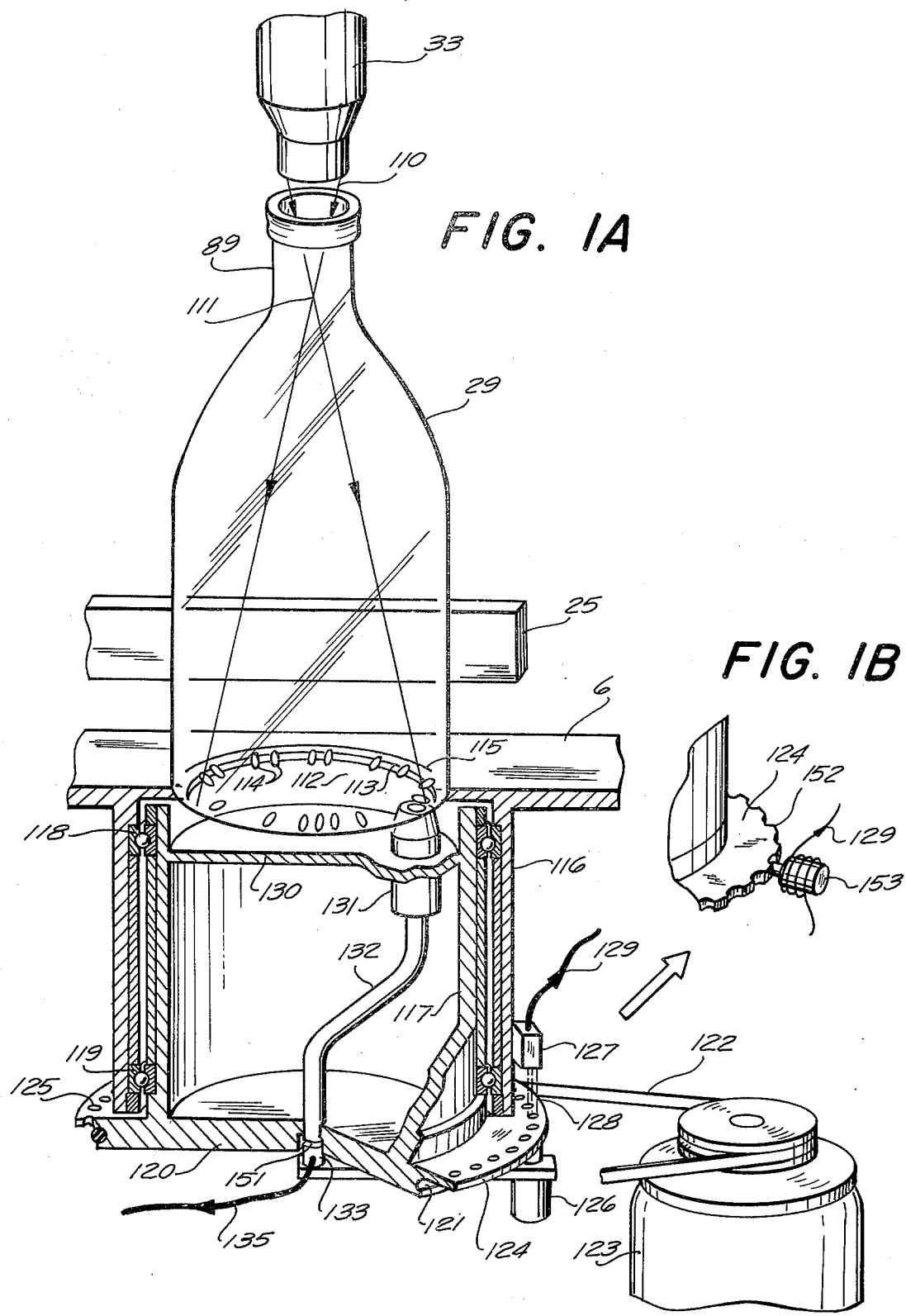

According to the embodiment of the present invention shown in FIG. 1 a bottle 29 is shown standing still and held by pressure against a support bracket 25 by means of a not shown holding device. Through the bottle neck 89 a converging light beam 110 is transmitted by means of a lamp with lens system 33. The light beam 110 converges towards a point 111 positioned at or close to the bottle neck 89 whereby the entire bottom of the bottle is lit up. Along a bottom circle 113 concentric with the bottle body 29 there are a number of lenses 114 arranged such that they are an integral part of the bottom glass 112 itself. In the slide strip 6 there is cut a circular hole 115, which is somewhat smaller than the diameter of the bottle 29. Underneath the slide strip 6 there is mounted a mould number reader casing 116' inside which a cylindrical mould number reader 117 is rotably mounted by means of ball bearings 118 and 119. The cylindrical mould number reader 117 is at its lower part equipped with a disc shaped base 120, which is provided with a belt groove 121 for the rotation of the rotably mounted mould number reader 117 by means of a belt 122 and a motor 123. The base 120 is further provided with a flange 124, which is equipped with a great number of concentrically positioned holes 125, which from the one side are illuminated by a lamp 126. At the other side of the flange 124 there is arranged a detector 127 for the reception of light pulses 128, which after detection are converted to electrical signals transmitted via wire 129. The mould number reader 117 is provided with an upper intermediate wall 130 in which a lens system 131 with short focal distance is mounted. The use of convex lenses in the bottom of the bottle will concentrate the penetrating light to a focal plane a short distance below the bottom. The lens system or reading head 131 will then produce a picture at the entrance surface of a fiber optic tube 132, which leads the light to the centre of the bottom plate 120, where a light sensitive detector 133 is mounted in a commutator type bearing such that it does not follow the rotation of the reading head 131.

From the detector 133 the output signals are then routed to the electronic unit via conductor 35 and then on to a suitable evaluation means e.g. a computer.

As shown in FIG. 2A the lenses 114 may e.g. be convex and cylindrical, while lenses 135 shown in FIG. 2B are concave and cylindrical. Every lens 114 in the bottom of the bottle 112 are positioned along a circle 113, as shown in FIG. 3.

The above described example functions in the following manner: When a bottle 29 by means of a not shown advancing member is brought to a stand still in approximately the proper position at the inspection station a not shown holding device with e.g. two wheels pressing the bottle 29 against the support bracket 25, such that the bottle will be placed in the exact position concentrically located in relation to the lens system 33 and the reader 117. Devices suitable for the purpose are disclosed in copending application Ser. No. 476,602 filed June 5, 1974 now Pat. No. 3,923,158. By means of a converging beam 110 the lamp with its lenses 33 will light up the entire bottom 112 by focusing the beam to a point 111 which beam will then diverge towards the bottom of the bottle 112. The motor 123 keeps the reader 117 in continuous rotation such that the lens system 131 quickly moves around and along the annular circle 113 catching all the light pulses which the lenses 114 are causing. These light pulses are routed via fiber optic tube 132 downwards to the lower centre of the reader 117, where a detector 133 converts the light pulses into electrical signals.

When a bottle 29 is in position for number reading a not shown position disc with impulse generator connected to the feeding means will give an impulse to the computer that number reading is to take place.

To enable the computer to register the instantaneous angular position of the reader 117 a multitude of holes 125, e.g. 240 holes are arranged in the flange 124, such that the lamp 126 gives a light pulse to the detector 127 every time a hole 125 is passing (see FIG. 1B). These light position pulses are converted in the detector 127 to electrical position pulses, which continueously via wire 129 are feed to the evaluating means. In order to make the reader 117 insensitive to the random positioning of the bottle at the inspection station the annular circle 113 of the bottom of the bottle 29 may be provided with a particular lens combination 134 (see FIG. 3) at which the reading is to commence, e.g. four lenses may be placed close together. This means that the computer must receive four pulses in rapid succession in order to start reading process. If the holes 125 are, e.g. 1.5° spaced from one another it may be of advantage to space the lenses 114 in the bottom 112 of the bottle further apart, e.g. at an angle 8 times larger, i.e. 12°. One may introduce 30 characters at the most on every turn and the counter of the evaluating means will then count eight positional pulses after the passage of the starting lenses and then immediately after the 8th pulse read the output of the detector 133. Is a lens present 12° from the starting point a "one" will be registered otherwise a " zero". After eight new positional pulses the sequence will be repeated and another "one" or "zero" will be registered etc.

This method implies that 30 binary characters may be moulded into the bottom 112 of the bottle 29. These 30 characters may preferably be scanned more than once in order to increase the accuracy and hereby may also a suitable self correcting code with parity characters be used. The rotation velocity of the reader should be made high enough to complete 2-3 turns during the tenth of a second, that the bottle 29 is at a stand still, e.g. an approximate rotation velocity of 1800 r/m.

The positional pulses may also be generated magnetically if the perepheral flange 124 is instead provided with (magnetic) cams, which may be part of a magnetic circuit of an external coil for generating, one voltage pulse at the passage of every cam (see FIG. 1B). According to another variation of the present invention shown in FIG. 2B, the lenses 135 in the bottom 112 of the bottle may be made concave, such that every character in the bottom of the bottle will correspond to a zero pulse at the output of the detector 133.

Figure 4A:
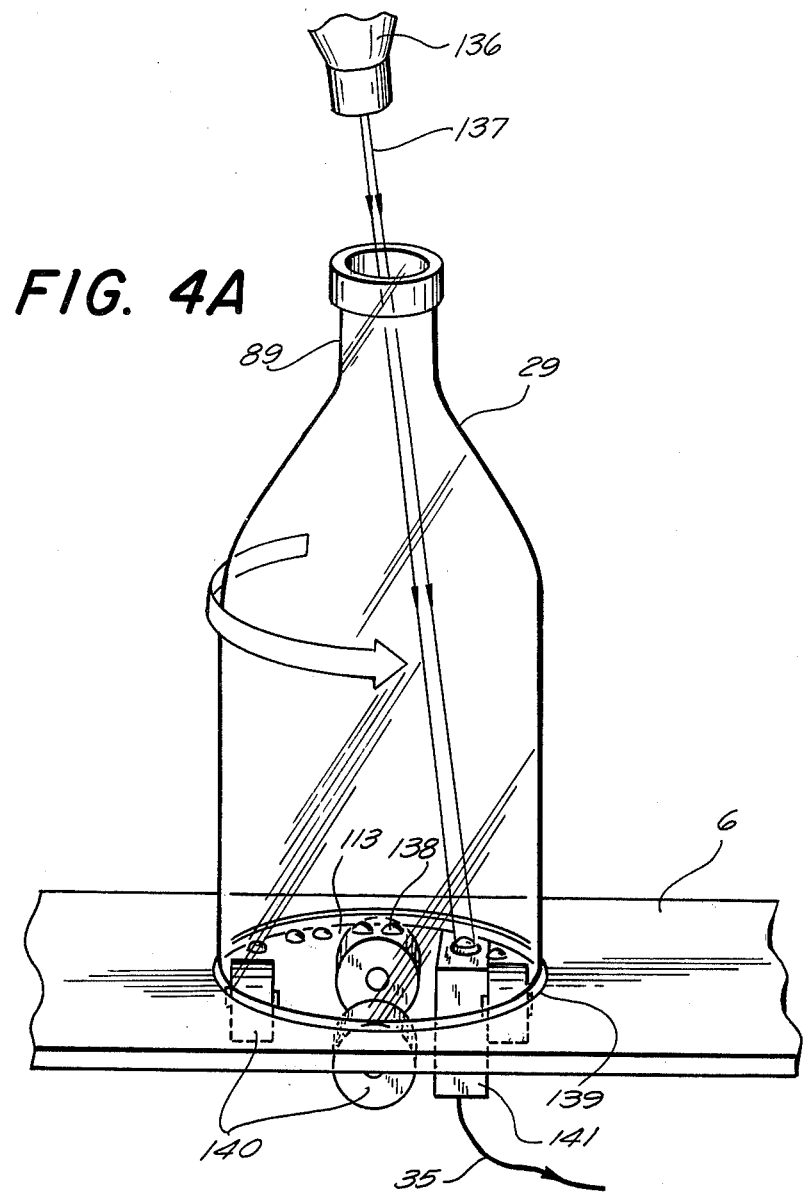
FIG. 4A shows a sectional view of a rotating bottle with spherical lenses and FIG. 4B shows an enlargement of such lens.

According to another embodiment of the present invention, as shown in FIG. 4A, the bottle 29 may be brought to rotate at the inspection station where a lamp with lenssystem 136 is sending a narrow cylindrical or slightly concentric light beam 137 down through the neck 89 of the bottle 29 and directed against that bottom ring 113 along which a row of spherical lenses 138 with radius R (see FIG. 4B) are moulded into the bottom of the bottle and where every lens also in this case corresponds to one character. To easily rotate to bottle 29 a well matched hole 139 is cut in the slide strip 6 in which hole a number of rollers 140 are arranged for contact with and rolling against the bottom 112 of the bottle 29. In this set up the hole 139 is matched to the side- and bottom shape of the bottle such that the bottle 29 will evenly and securely rotate around its axis without sidejumps, which may interfere with the operation of the detector 141. Detector 141 is arranged and rigidly mounted under the bottom 112 of the bottle right underneath the bottom ring 113. The spherical lenses arranged in the bottom 112 of the bottle may, as shown in FIG. 4B, be given a suitable radius R with respect to lightdeflection and material strength.

The device as shown in FIG. 4A functions such that the bottle 29 is immediately upon arrival put into rapid rotation by means of a not shown member. The bottle 29 stands at rollers 140 arranged in a hole 139 of the slide strip 6 and by certain devices the bottle 29 is made to rotate around its own axis without jerking sideways which may cause faulty readings. The narrow beam 137 from the lamp system 136 illuminates then the bottom ring 113 whereby a fixed detector reads a starting mark, whereupon the reading proper starts. The reader 141 thus becomes insensitive to the random start position of bottle. In this embodiment it may be of advantage to let the driving device for the bottle also provide required positional pulses to the computer. Besides the reading takes place according to the same principle as does the reader of FIG. 1A.

Figure 4B:
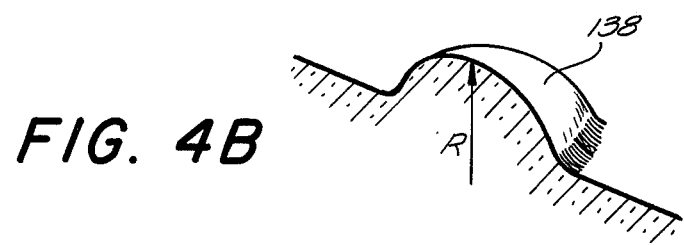

FIG. 4B shows a variation of the present invention according to which the spherical lenses 138 may be made concave and be illuminated with diffused light. Possibly reflected light may be used at the reception such that both light source and detector may be positioned underneath the bottom of the bottle.

Figure 5A:
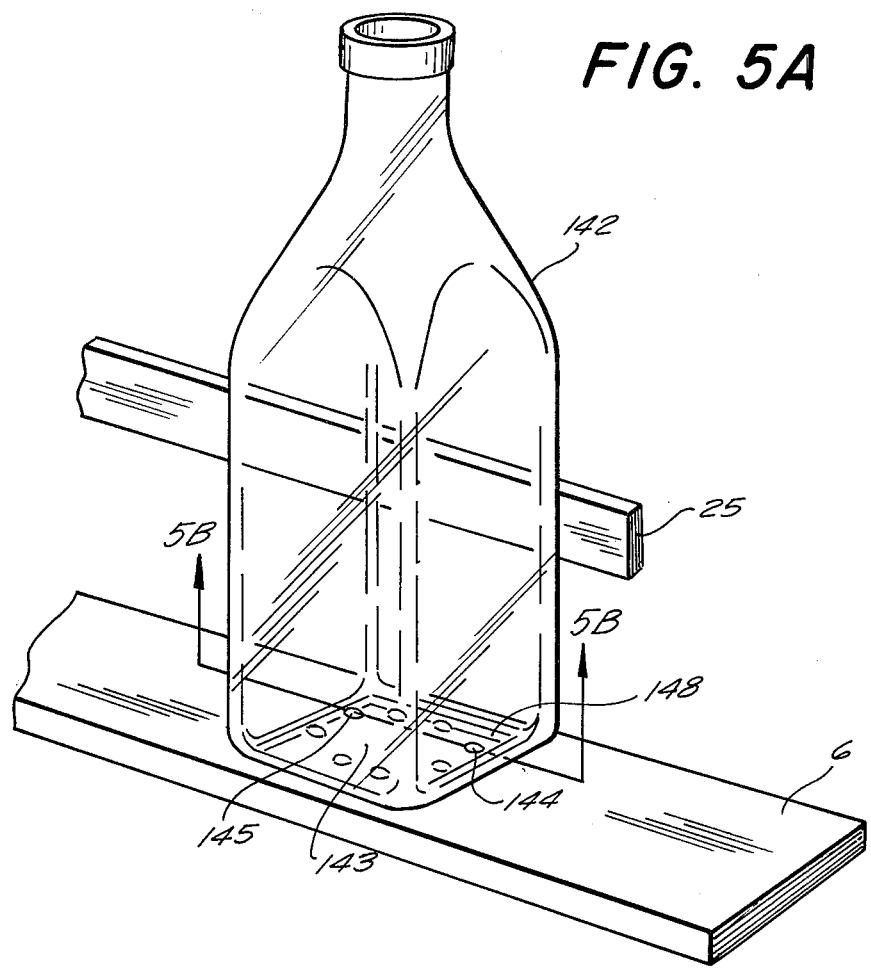
FIG. 5A shows a square bottle with recesses in its bottom for mechanical contacts
Figure 5B:
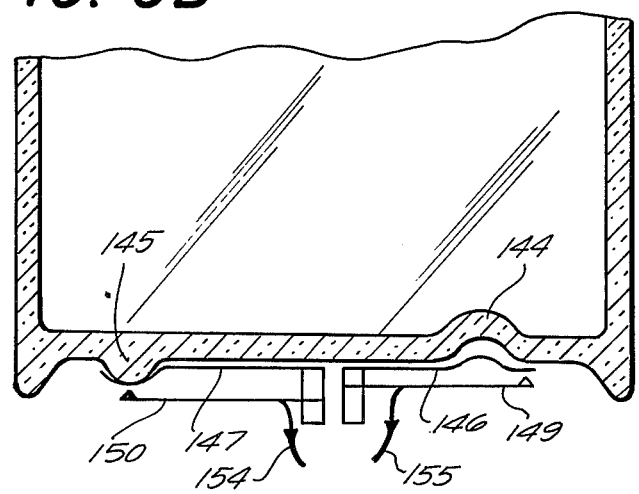
FIG. 5B shows a portion of the bottle of FIG. 5A.

According to another example of the present invention as shown in FIG. 5A the bottle 142 may be square and at its bottom 143 equipped with resessions 144 or projections 145 intended for co-operation with contact stacks 146 and 147 respectively (see FIG. 5B). Should one require a particular orientation of the bottle before it is placed at the inspection station a not shown orientation device must be mounted at the inspection station. It should, however, be easier to position the bottom characters 144 and 145 in a symmetrical way, as shown by FIG. 5A, and then to arrange the reading code such that a certain character combination corresponds to the starting mark. One may, e.g. choose eight characters 144 and 145 in a certain combination at the bottom 143 of the bottle. FIG. 5B shows a sectional view of the lower part of the bottle through the characters 144 and 145, which may be given a suitable shape for co-operation with the contact pairs 146-149 and 147-150. The contact pairs 146-149 must here be designed such that they are not harmed but yield if a projecting sign 145 appears at the place of the sign 144.

The device shown in FIG. 5A functions such that when the bottle 142 with or without prior orientation has arrived at the station, it is pressed backwards and downwards partly against the support bracket 25 and partly against the underlaying contacts 147-150. The eight contacts will then either remain in there original position or change position by contact either with a projection 145 or a recession 144. These positional changes may then electrically be conveyed to an evaluation means, which may identify the present combination of contact positions, which according to a certain agreed code will reveal information regarding the bottle 142. It is here quite obvious that the contacts 147-150 may be substituted by micro switches or other easily activated pulse emitting means.

The marking of the bottles may be accomplished in other ways, such as the moulding into the glass of black or coloured crystals or of radio active elements.

Figure 6:
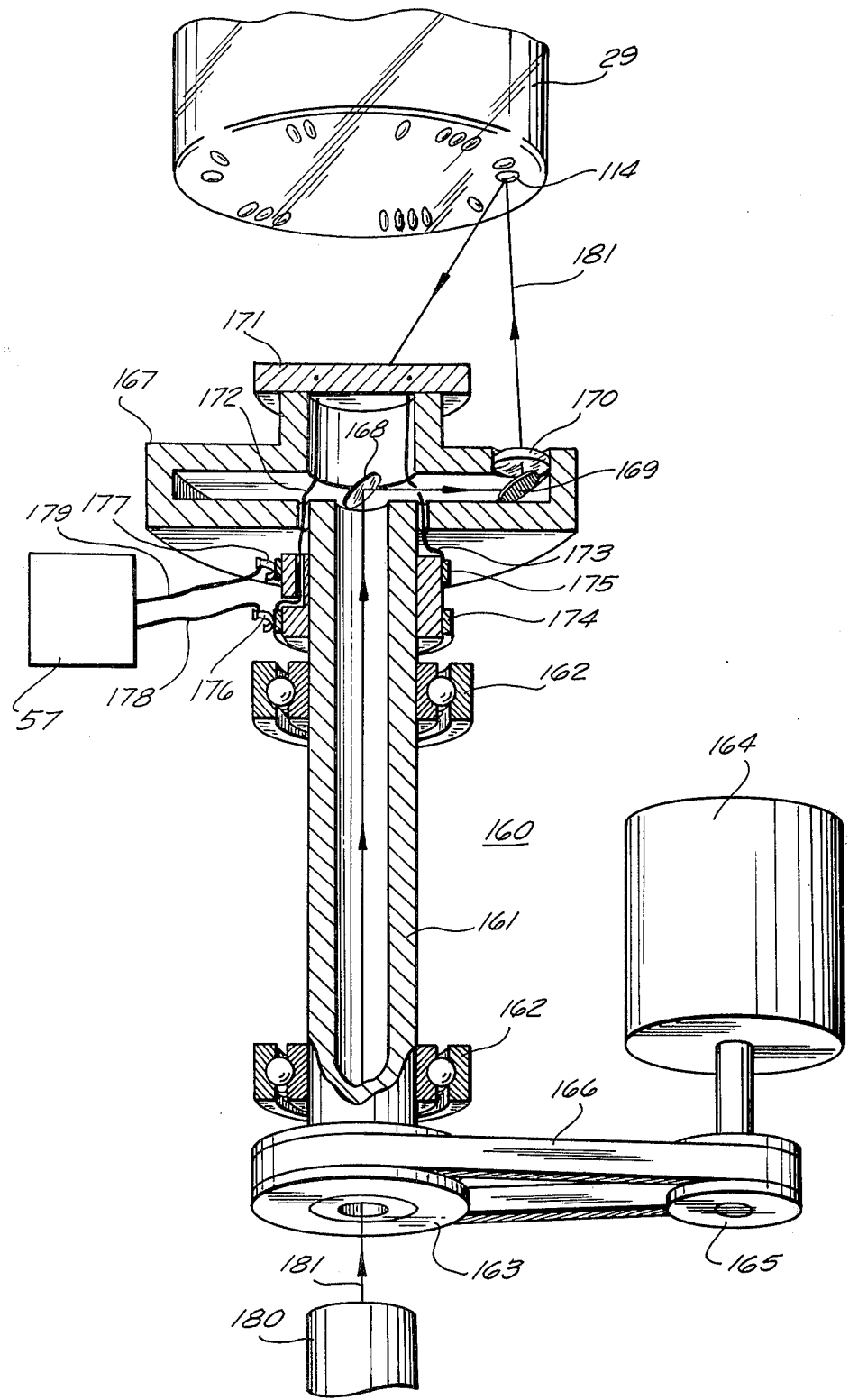
FIG. 6 shows a rotating optical mould number reader using reflected light.

According to another embodiment of the present invention, see FIG. 6, a mould number reader 160 is shown, which uses a rotating light beam, e.g. a laser beam, for the scanning of the bottom lenses of the bottle. Hereby a rotable, hollow shaft 161 is used, which shaft is provided with two bearings 162 and a pulley 163 driven by a motor 164 with a corresponding pulley 165 and a belt 166. The hollow shaft 161 is further provided with a mountingflange for the mirrors 168 and 169 and for a cylinder lens 170 and a photo-sensitive element 171. The photo-sensitive element 171 yields at constant illumination a constant ouput voltage, which via conductors 172 and 173 are each fed to its own contact ring 174 and 175. Each of these rotates in contact with a slip-ring 176 and 177 for conveying said voltage to the electronic unit 57 via conductors 178 and 179.

The above described device functions in such a way that a light source 180 emits a very concentrated lightbeam 181 coaxially with a hollow shaft 161. The beam thus hits the mirror 168, which is mounted at the centre of the flange 167, whereby the beam is reflected towards the mirror 169 mounted at the rim of the flange 167. The beam is now reflected again by the mirror 169 against the ring 113 of marks 114 which are moulded into the resting bottle 29. If no mark is present at the point where the beam is falling, the beam 181 is reflected back towards the photo-sensitive element 171, which for at a constantly hitting beam will generate a constant voltage, which via conveyence means 172-179 (possibly of inductive type) will carry the signals on to the electronic unit 57 for decoding.

When the motor 164 is now started the hollow shaft 161 will start rotating and the beam 181 will scan the bottom circle 113 of the bottle 29 with marks 114. Every time a mark 114 in the form of a lens is hit by the lightbeam 181 this will be reflected in another direction and a zero pulse will be present in the output voltage. Tests have shown that from an operational point of view it may be more favourable to feed out signals derived from voltage changes with inductive means. The pulses received by the evaluating means or electronic unit 57 are then decoded and the bottle is thus identified.

A further embodiment of the present invention, which is not shown utilizes a rotating bottle with marks in its bottom surface, which marks are scanned by means of mechanical contacts.

In another embodiment according to the present invention one may exclude the ring 113 and position the character marks 145 according to an arbitraty arrangement for contact with pulse emitting means.

Even if the present invention has been described by a limited number of examples only, it must be assumed, that other embodiments and combinations as well may fall within the scope of the invention.

We claim:
1. Apparatus for identifying which of a plurality of moulds moulded a particular light transparent container comprising containers formed by the moulds, each container having integrally moulded in a line along its bottom a coded combination of lens members for focussing light projected onto the inner surface of the bottom of the container to a focal plane opposite the outer surface of the bottom of the container, each of said coded combinations being associated with a different mould; light source means for projecting light onto said inner surface of the bottom of the container; light detector means including a short focus objective lens focused at said focal plane, a photo-sensitive transducer for generating signals whose amplitude is a function of received light, guiding means for guiding light from said short focus objective lens to said photo-sensitive transducer and means for emitting a pulse each time the generated signal exceeds a given amplitude; and moving means for causing a relative movement along said line between said lens members and said short focus objective lens.

2. The apparatus of claim 1 wherein said inner surface is uniformly illuminated.

3. The apparatus of claim 1 wherein said container remains stationary and said moving means moves said short focus objective lens.

4. The apparatus of claim 3 wherein said lens members are arrayed on a circle concentric with the axis of the container and said moving means moves said short focal length lens along a path colinear with said circle.

5. The apparatus of claim 1 wherein said lens members are moulded along a circle in the bottoms of the containers, wherein said light source means projects a beam of light to a particular point on the circle on the inner surface of the bottom of a container, wherein said light detector means includes a short focus objective lens focus at a point in said focal plane opposite the point of impingement of the beam of light and wherein said moving means includes means for rotating a container about its axis.

* * * * *